(12) United States Patent
Patel

(10) Patent No.: US 7,449,058 B2
(45) Date of Patent: Nov. 11, 2008

(54) PHTHALOCYANINES AND THEIR USE IN INK-JET PRINTERS

(75) Inventor: Prakash Patel, Manchester (GB)

(73) Assignee: Fujifilm Imaging Colorants Limited, Manchester (GB)

( * ) Notice: Subject to any disclaimer, the term of this patent is extended or adjusted under 35 U.S.C. 154(b) by 253 days.

(21) Appl. No.: 11/326,456

(22) Filed: Jan. 6, 2006

(65) Prior Publication Data

US 2006/0162615 A1  Jul. 27, 2006

(30) Foreign Application Priority Data

Jan. 21, 2005  (GB) .................. 0501275.2

(51) Int. Cl.
*C09D 11/00* (2006.01)
*C09D 11/02* (2006.01)
*C09B 47/04* (2006.01)
*B41J 2/01* (2006.01)

(52) U.S. Cl. ............... 106/31.49; 540/133; 347/100; 8/661

(58) Field of Classification Search ............ 106/31.49; 540/133; 347/100; 8/661
See application file for complete search history.

(56) References Cited

U.S. PATENT DOCUMENTS

| | | | | |
|---|---|---|---|---|
| 4,952,688 | A | 8/1990 | Springer | 540/134 |
| 6,569,212 | B2 | 5/2003 | Carr | 8/445 |
| 7,014,696 | B2 * | 3/2006 | Patel | 106/31.49 |
| 7,022,171 | B2 * | 4/2006 | Patel et al. | 106/31.49 |
| 7,147,698 | B2 * | 12/2006 | Patel | 106/31.49 |
| 7,156,908 | B2 * | 1/2007 | Patel | 106/31.49 |
| 7,182,806 | B2 * | 2/2007 | Patel | 106/31.49 |
| 7,189,283 | B2 * | 3/2007 | Patel | 106/31.49 |
| 2007/0006772 | A1* | 1/2007 | Fujii et al. | 106/31.49 |

FOREIGN PATENT DOCUMENTS

| | | | |
|---|---|---|---|
| EP | 1607445 | * | 12/2005 |
| WO | WO 2004/085541 | * | 10/2004 |

* cited by examiner

*Primary Examiner*—Helene Klemanski
(74) *Attorney, Agent, or Firm*—Morgan Lewis & Bockius LLP

(57) ABSTRACT

A composition comprising:
(a) a major dye component which is a mixture of phthalocyanine dyes of Formula (1) and salts thereof:

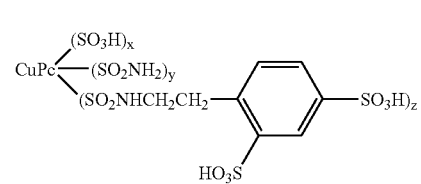

Formula (1)

wherein:
Pc represents a phthalocyanine nucleus of formula;

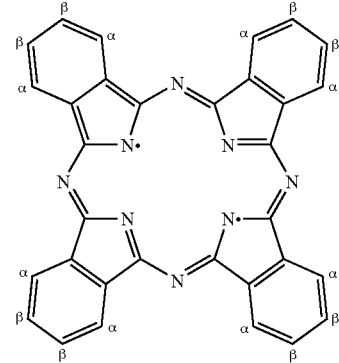

x is 0.1 to 3.8;
y is 0.1 to 3.8;
z is 0.1 to 3.8;
the sum of x+y+z is 3 to 4; and
the substituents, represented by x, y and z, are attached only to a β-position on the phthalocyanine ring; and
(b) a liquid medium.
Also ink-jet inks and cartridges, printing processes, printed material and dye mixtures.

18 Claims, No Drawings

PHTHALOCYANINES AND THEIR USE IN INK-JET PRINTERS

This invention relates to compositions, to dyes, to printing processes, to printed substrates and to ink-jet printer cartridges.

Ink-jet printing is a non-impact printing technique in which droplets of ink are ejected through a fine nozzle onto a substrate without bringing the nozzle into contact with the substrate.

Colour ink-jet printers typically use four inks of differing hues: magenta, yellow, cyan, and black. Colours other than these may be obtained using differing combinations of these inks. Thus, for optimum print quality, the colourants used must be able to form an ink with a specific precise hue. This can be achieved by mixing colourants but is advantageously achieved using a single colourant with the exact hue required.

With the advent of high-resolution digital cameras and ink-jet printers it is becoming increasingly common to print off photographs using an ink-jet printer. This avoids the expense of conventional silver halide photography and provides a print quickly and conveniently.

While ink-jet printers have many advantages over other forms of printing and image development there are still technical challenges to be addressed. For example, there are the contradictory requirements of providing ink colorants that are soluble in the ink medium and yet do not run or smudge excessively when printed on paper. The inks need to dry quickly to avoid sheets sticking together after they have been printed, but they should not form a crust over the tiny nozzle used in the printer. Storage stability is also important to avoid particle formation that could block the tiny nozzles used in the printer. Furthermore, the resultant images should not fade rapidly on exposure to light or common oxidising gases such as ozone.

Most cyan colorants used in ink-jet printing are based on phthalocyanines and problems of fading and shade change are particularly acute with dyes of this class.

Thus, the present invention provides a composition comprising:

(a) a major dye component which is a mixture of phthalocyanine dyes of Formula (1) and salts thereof:

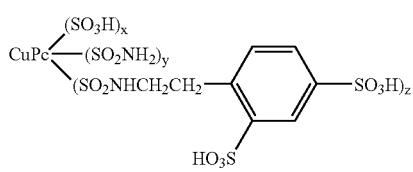

Formula (1)

wherein:

Pc represents a phthalocyanine nucleus of formula;

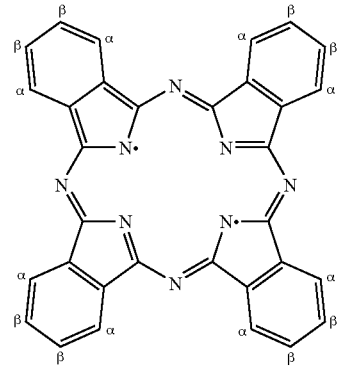

x is 0.1 to 3.8;

y is 0.1 to 3.8;

z is 0.1 to 3.8;

the sum of x+y+z is 3 to 4; and the substituents, represented by x, y and z, are attached only to a β-position on the phthalocyanine ring; and (b) a liquid medium.

Phthalocyanine dyes bearing sulfo, sulfonamide and substituted sulfonamide substituents are usually prepared by sulfonating a phthalocyanine pigment followed by chlorination and then amination/amidation. The product of this reaction is a complex mixture which carries sulfo, sulfonamide and substituted sulfonamide substituents in any susceptible position on the phthalocyanine ring (for example see Schofield, J and Asaf, M in Journal of Chromatography, 1997, 770, pp 345-348).

The mixture of dyes of Formula (1) are preferably prepared by means of a cyclisation reaction comprising a β-substituted phthalic acid or analogue thereof. Preferred β-substituted phthalic acid analogues are selected from the group consisting of phthalonitrile, iminoisoindoline, phthalic anhydride, phthalimide and phthalamide or mixtures thereof.

The cyclisation reaction is carried out in the presence of a suitable source of ammonia (if required), a suitable copper salt, for example $CuCl_2$, and a base such as 1,8-diazabicyclo[5.4.0]undec-7-ene (DBU) followed by, if required, further synthetic steps, for example, chlorination and then amination/amidation.

The total amount of x+y+z may be controlled by varying the ratio of substituted phthalic acid or analogue thereof to unsubstituted phthalic acid or analogue thereof. Thus, when only β-substituted phthalic acid or a β-substituted analogue thereof is used in the cyclisation reaction then x+y+z is 4.

Preferably phthalocyanine dyes of Formula (1) where the sulfo, sulfonamide and substituted sulfonamide substituents are attached to a β-position on the phthalocyanine ring are prepared by a process which comprises the cyclisation of phthalic acid or an analogue thereof bearing a sulfo group in a β-position, a cyclisation which comprises 4-sulfophthalic acid is particularly preferred.

It is especially preferred that the cyclisation is carried out with 4-sulfophthalic acid in the presence of a nitrogen source, such as urea, a copper salt, such as $CuCl_2$, and a base such as 1,8-diazabicyclo[5.4.0]undec-7-ene (DBU) to give phthalocyanine β-tetrasulfonic acid. The phthalocyanine β-tetrasulfonic acid is then chlorinated and the sulfonyl chloride groups so formed are reacted with ammonia and aminoethylbenzene-2,4-disulfonic acid (conveniently prepared by sulfonation of 2-aminoethylbenzene with 30% oleum). This reaction is preferably performed in water at a pH above 7. Typically the reaction is performed at a temperature of 30 to 70° C. and is usually complete in less than 24 hours. Ammonia and aminoethylbenzene-2,4-disulfonic acid may be used as a mixture or added sequentially.

The ratio of sulfo to sulfonamide substituents may be varied by varying the nature and amount of chlorinating agent used, the relative amounts of ammonia and aminoethylbenzene-2,4-disulfonic acid and the reaction conditions in both reactions.

A skilled person will appreciate that the product of these reactions will be a disperse mixture and so the values of x, y and z will represent an average of the groups present in the mixture.

When phthalocyanine β-tetrasulfonic acid is an intermediate in a route to dyes of Formula (1) it may be chlorinated by reacting with any suitable chlorinating agent.

Chlorination is preferably carried out by treating the phthalocyanine β-tetrasulfonic acid with chlorosulfonic acid preferably in the presence of an acid halide such as thionyl chloride, sulfuryl chloride, phosphorous pentachloride, phosphorous oxychloride and phosphorous trichloride.

Preferably x has a value of 0.2 to 3.0, more preferably 0.3 to 2, especially 0.4 to 1.5 and more especially 0.5 to 1.

Preferably y has a value of 0.2 to 2, more preferably y has a value of 0.25 to 0.9 and especially of 0.3 to 0.8.

Preferably z has a value of 0.5 to 3.5, more preferably 1 to 3.4 and especially 2.2 to 3.2.

Preferably x+y+z is 4.

Acid groups on the dyes of Formula (1) are preferably in the form of a salt. Thus, the Formulae shown herein include the dyes in free acid and in salt form.

Preferred salts are alkali metal salts, especially lithium, sodium and potassium, ammonium and substituted ammonium salts (including quaternary amines such as $((CH_3)_4N^+)$ and mixtures thereof. Especially preferred are salts with sodium, lithium, ammonia and volatile amines, more especially sodium salts. The dyes may be converted into a salt using known techniques.

The dyes of Formula (1) may exist in tautomeric forms other than those shown in this specification. These tautomers are included within the scope of the present invention.

When the preferred route, as set out above, is used to synthesise dyes of Formula (1) then they are predominantly formed as ammonium salts. However, any known techniques may be used to exchange ammonia for another cation for example, acidification, optionally followed by dialysis, to remove the original cations with subsequent addition of alternative cations (e.g. by addition of alkali metal hydroxide, ammonium salt or amine). Use of ion exchange resins and reverse osmosis are other well-known techniques for cation exchange.

Preferred compositions according to the invention comprise:
(a) from 0.01 to 30 parts of a compound of Formula (1); and
(b) from 70 to 99.99 parts of a liquid medium;

wherein all parts are by weight

Preferably the number of parts of (a)+(b)=100.

The number of parts of component (a) is preferably from 0.1 to 20, more preferably from 0.5 to 15, and especially from 1 to 5 parts. The number of parts of component (b) is preferably from 80 to 99.9, more preferably from 85 to 99.5 and especially from 95 to 99 parts.

Preferably component (a) is completely dissolved in component (b). Preferably component (a) has a solubility in component (b) at 20° C. of at least 10%. This allows the preparation of liquid dye concentrates that may be used to prepare more dilute inks and reduces the chance of the dye precipitating if evaporation of the liquid medium occurs during storage.

The inks may be incorporated in an ink-jet printer as a high concentration cyan ink, a low concentration cyan ink or both a high concentration and a low concentration ink. In the latter case this can lead to improvements in the resolution and quality of printed images. Thus the present invention also provides a composition (preferably an ink) where component (a) is present in an amount of 2.5 to 7 parts, more preferably 2.5 to 5 parts (a high concentration ink) or component (a) is present in an amount of 0.5 to 2.4 parts, more preferably 0.5 to 1.5 parts (a low concentration ink).

Preferred liquid media include water, a mixture of water and organic solvent and organic solvent free from water. Preferably the liquid media comprises a mixture of water and organic solvent or organic solvent free from water.

When the liquid medium (b) comprises a mixture of water and organic solvent, the weight ratio of water to organic solvent is preferably from 99:1 to 1:99, more preferably from 99:1 to 50:50 and especially from 95:5 to 80:20.

It is preferred that the organic solvent present in the mixture of water and organic solvent is a water-miscible organic solvent or a mixture of such solvents. Preferred water-miscible organic solvents include $C_{1-6}$alkanols, preferably methanol, ethanol, n-propanol, isopropanol, n-butanol, sec-butanol, tert-butanol, n-pentanol, cyclopentanol and cyclohexanol; linear amides, preferably dimethylformamide or dimethylacetamide; ketones and ketone-alcohols, preferably acetone, methyl ether ketone, cyclohexanone and diacetone alcohol; water-miscible ethers, preferably tetrahydrofuran and dioxane; diols, preferably diols having from 2 to 12 carbon atoms, for example pentane-1,5-diol, ethylene glycol, propylene glycol, butylene glycol, pentylene glycol, hexylene glycol and thiodiglycol and oligo- and poly-alkyleneglycols, preferably diethylene glycol, triethylene glycol, polyethylene glycol and polypropylene glycol; triols, preferably glycerol and 1,2,6-hexanetriol; mono-$C_{1-4}$-alkyl ethers of diols, preferably mono-$C_{1-4}$-alkyl ethers of diols having 2 to 12 carbon atoms, especially 2-methoxyethanol, 2-(2-methoxyethoxy)ethanol, 2-(2-ethoxyethoxy)-ethanol, 2-[2-(2-methoxyethoxy)ethoxy]ethanol, 2-[2-(2-ethoxyethoxy)-ethoxy]-ethanol and ethyleneglycol monoallylether; cyclic amides, preferably 2-pyrrolidone, N-methyl-2-pyrrolidone, N-ethyl-2-pyrrolidone, caprolactam and 1,3-dimethylimidazolidone; cyclic esters, preferably caprolactone; sulfoxides, preferably dimethyl sulfoxide and sulfolane. Preferably the liquid medium comprises water and 2 or more, especially from 2 to 8, water-miscible organic solvents.

Especially preferred water-miscible organic solvents are cyclic amides, especially 2-pyrrolidone, N-methyl-pyrrolidone and N-ethyl-pyrrolidone; diols, especially 1,5-pentane diol, ethyleneglycol, thiodiglycol, diethyleneglycol and triethyleneglycol; and mono-$C_{1-4}$-alkyl and $C_{1-4}$-alkyl ethers of diols, more preferably mono-$C_{1-4}$-alkyl ethers of diols having 2 to 12 carbon atoms, especially 2-methoxy-2-ethoxy-2-ethoxyethanol.

Examples of further suitable liquid media comprising a mixture of water and one or more organic solvents are described in U.S. Pat. No. 4,963,189, U.S. Pat. No. 4,703,113, U.S. Pat. No. 4,626,284 and EP-A-425,150.

When the liquid medium comprises organic solvent free from water, (i.e. less than 1% water by weight) the solvent preferably has a boiling point of from 30° to 200° C., more preferably of from 40° to 150° C., especially from 50 to 125° C. The organic solvent may be water-immiscible, water-miscible or a mixture of such solvents. Preferred water-miscible organic solvents are any of the hereinbefore-described water-miscible organic solvents and mixtures thereof. Preferred water-immiscible solvents include, for example, aliphatic hydrocarbons; esters, preferably ethyl acetate; chlorinated hydrocarbons, preferably $CH_2Cl_2$; and ethers, preferably diethyl ether; and mixtures thereof.

When the liquid medium comprises a water-immiscible organic solvent, preferably a polar solvent is included because this enhances solubility of the mixture of phthalocyanine dyes in the liquid medium. Examples of polar solvents include $C_{1-4}$-alcohols.

In view of the foregoing preferences it is especially preferred that where the liquid medium is organic solvent free from water it comprises a ketone (especially methyl ethyl ketone) and/or an alcohol (especially a $C_{1-4}$-alkanol, more especially ethanol or propanol).

The organic solvent free from water may be a single organic solvent or a mixture of two or more organic solvents. It is preferred that when the liquid medium is organic solvent free from water it is a mixture of 2 to 5 different organic solvents. This allows a liquid medium to be selected that gives good control over the drying characteristics and storage stability of the ink.

Liquid media comprising organic solvent free from water are particularly useful where fast drying times are required and particularly when printing onto hydrophobic and non-absorbent substrates, for example plastics, metal and glass.

The liquid media may of course contain additional components conventionally used in ink-jet printing inks, for example viscosity and surface tension modifiers, corrosion inhibitors, biocides, kogation reducing additives and surfactants which may be ionic or non-ionic.

Although not usually necessary, further colorants may be added to the ink to modify the shade and performance properties. Examples of such colorants include C.I. Direct Yellow 86, 132, 142 and 173; C.I. Direct Blue 307; C.I. Food Black 2; C.I. Direct Black 168 and 195; and C.I. Acid Yellow 23.

It is considered that a mixture of phthalocyanine dyes is a major dye component if a skilled man in ink formulation would purposely select that specific dye mixture to give a particular colour effect. Thus, in the composition of the present invention it is expected that of least 50% of the total amount of the cyan dye in the composition would be a mixture of phthalocyanine dyes of Formula (1).

If the composition of the present invention contains phthalocyanine dyes other than those of Formula (1) then preferably at least 70% by weight, more preferably at least 80% by weight, especially at least 90% by weight, more especially at least 95% by weight and particularly at least 99% by weight of the total amount of phthalocyanine dye is of Formula (1) wherein the substituents, represented by x, y and z are attached to a β position on the phthalocyanine ring.

It is preferred that the composition according to the invention is ink suitable for use in an ink-jet printer. Ink suitable for use in an ink-jet printer is ink which is able to repeatedly fire through an ink-jet printing head without causing blockage of the fine nozzles.

Ink suitable for use in an ink-jet printer preferably has a viscosity of less than 20 cP, more preferably less than 10 cP, especially less than 5 cP, at 25° C.

Ink suitable for use in an ink-jet printer preferably contains less than 500 ppm, more preferably less than 250 ppm, especially less than 100 ppm, more especially less than 10 ppm in total of divalent and trivalent metal ions (other than any divalent and trivalent metal ions bound to a colorant of Formula (1) or any other component of the ink).

Preferably ink suitable for use in an ink-jet printer has been filtered through a filter having a mean pore size below 10 μm, more preferably below 3 μm, especially below 2 μm, more especially below 1 μm. This filtration removes particulate matter that could otherwise block the fine nozzles found in many ink-jet printers.

Preferably ink suitable for use in an ink-jet printer contains less than 500 ppm, more preferably less than 250 ppm, especially less than 100 ppm, more especially less than 10 ppm in total of halide ions.

A second aspect of the invention provides a process for forming an image on a substrate comprising applying ink suitable for use in an ink-jet printer, according to the first aspect of the invention, thereto by means of an ink-jet printer.

The ink-jet printer preferably applies the ink to the substrate in the form of droplets that are ejected through a small orifice onto the substrate. Preferred ink-jet printers are piezoelectric ink-jet printers and thermal ink-jet printers. In thermal ink-jet printers, programmed pulses of heat are applied to the ink in a reservoir by means of a resistor adjacent to the orifice, thereby causing the ink to be ejected from the orifice in the form of small droplets directed towards the substrate during relative movement between the substrate and the orifice. In piezoelectric ink-jet printers the oscillation of a small crystal causes ejection of the ink from the orifice. Alternately the ink can be ejected by an electromechanical actuator connected to a moveable paddle or plunger, for example as described in International Patent Application WO00/48938 and International Patent Application WO00/55089.

The substrate is preferably paper, plastic, a textile, metal or glass, more preferably paper, an overhead projector slide or a textile material, especially paper.

Preferred papers are plain or treated papers which may have an acid, alkaline or neutral character. Glossy papers are especially preferred.

A third aspect of the present invention provides a material preferably paper, plastic, a textile, metal or glass, more preferably paper, an overhead projector slide or a textile material, especially paper more especially plain, coated or treated papers printed with a composition according to the first aspect of the invention or by means of a process according to the second aspect of the invention.

It is especially preferred that the printed material of the third aspect of the invention is a photograph printed using an ink-jet printer.

A fourth aspect of the present invention provides an ink-jet printer cartridge comprising a chamber and an ink suitable for use in an ink-jet printer wherein the ink is in the chamber and the ink is as defined in the first aspect of the present invention. The cartridge may contain a high concentration ink and a low concentration ink, as described in the first aspect of the invention, in different chambers.

A fifth aspect of the present invention provides a mixture of phthalocyanine dyes of Formula (1) and salts thereof:

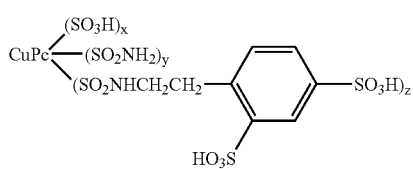

Formula (1)

wherein:
Pc represents a phthalocyanine nucleus of formula;

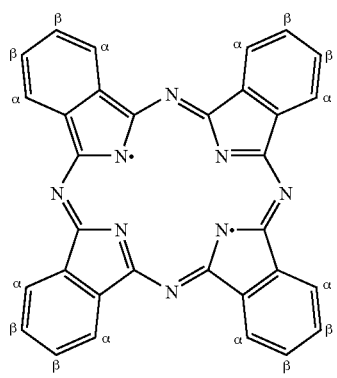

x is 0.1 to 3.8;
y is 0.1 to 3.8;
z is 0.1 to 3.8;
the sum of x+y+z is 3 to 4; and the substituents, represented by x, y and z, are attached only to a β-position on the phthalocyanine ring.

Preferences for x, y and z are as described in the first aspect of the invention.

Preferably the mixture of phthalocyanine dyes of Formula (1) according to the fifth aspect of the invention are prepared by means of a cyclisation reaction comprising a β-substituted phthalic acid or analogue thereof. Preferred β-substituted phthalic acid analogues are selected from the group consisting of phthalonitrile, iminoisoindoline, phthalic anhydride, phthalimide and phthalamide or mixtures thereof.

The cyclisation reaction is carried out in the presence of a suitable source of ammonia (if required), a suitable copper salt, for example $CuCl_2$, and a base such as 1,8-diazabicyclo[5.4.0]undec-7-ene (DBU) followed by, if required, further synthetic steps, for example, chlorination and then amination/amidation.

Preferably the mixture of phthalocyanine dyes of Formula (1) according to the fifth aspect of the invention, are prepared by cyclisation of 4-sulfophthalic acid and optionally phthalic acid.

It is especially preferred that the mixture of phthalocyanine dyes of Formula (1) according to the fifth aspect of the invention, are prepared by cyclisation of 4-sulfophthalic acid in the presence of a nitrogen source, such as urea, a copper salt, such as $CuCl_2$, and a base such as 1,8-diazabicyclo[5.4.0]undec-7-ene (DBU) to give phthalocyanine β-tetrasulfonic acid. The phthalocyanine β-tetrasulfonic acid is then chlorinated and the sulfonyl chloride groups so formed are reacted with ammonia and aminoethylbenzene-2,4-disulfonic acid (conveniently prepared by sulfonation of 2-aminoethylbenzene with 30% oleum). This reaction is preferably performed in water at a pH above 7. Typically the reaction is performed at a temperature of 30 to 70° C. and is usually complete in less than 24 hours. Ammonia and aminoethylbenzene-2,4-disulfonic acid may be used as a mixture or added sequentially.

A sixth aspect of the present invention provides a material preferably paper, plastic, a textile, metal or glass, more preferably paper, an overhead projector slide or a textile material, especially paper more especially plain, coated or treated papers printed with a mixture of phthalocyanine dyes of Formula (1) and salts thereof according to the fifth aspect of the invention.

The invention is further illustrated by the following Examples in which all parts and percentages are by weight unless otherwise stated.

EXAMPLE 1

Preparation of

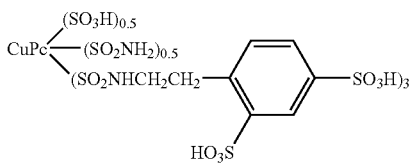

Stage 1 Preparation of 2'-aminoethylbenzene 2,4 disulphonic acid

Prepared by sulphonation of 2-aminoethylbenzene with 30% oleum.

Stage 2

Potassium 4-sulfophthalic acid (56.8 g), urea (120 g), $CuCl_2$ (6.9 g), ammonium molybdate (1.2 g) and 1,8-diazabicyclo[5.4.0]undec-7-ene (DBU) (7.5 g) were mixed in a reaction vessel. The mixture was then warmed in stages (130° C./30 minutes, 150° C./30 minutes, 180° C./30 minutes, 220° C./30 minutes) over 2 hours and the melt which formed was stirred at 220° C. for a further 2 hours. The solid which formed was extracted 4 times with hot water (4×200 ml) and the extract was filtered to remove insoluble material. The resultant filtrate was stirred at between 60° C.-70° C. and then sufficient NaCl was added to give a 7% salt solution. Stirring was continued and the solid that precipitated was filtered, washed with a 10% salt solution (200 ml) and pulled dry by vacuum. The resultant damp solid (77.6 g) was slurried in acetone, filtered and dried first at room temperature and then at 50° C.

Stage 3 Preparation of the Title Product

Phosphorous oxychloride (11.92 g) was added dropwise to chlorosulfonic acid (116.5 g) over 5-10 minutes while keeping the temperature below 30° C. When all the $POCl_3$ had been added, the product of stage 2 (22 g) was added portionwise while keeping the reaction temperature below 60° C., this addition took 20-30 minutes. The reaction mixture was stirred at 50-60° C. for 15-20 minutes. The temperature of the reaction mixture was then gradually increased to 138-140° C. over 30 minutes, held at this temperature for 6.5 h and then stirred overnight at room temperature. The mixture was added to water/ice/NaCl/concentrated HCl (120 ml/120 g/15 g/8 ml). The solid that precipitated was filtered, washed with ice cold acidified 5% salt solution and pulled dry using a vacuum pump. Half the resultant damp paste (43 g) in water (150 ml) was added to a mixture of 2'-aminoethylbenzene 2 4 disulphonic acid 80% (11.64 g) (from Stage 1), ammonia 35% w/w (0.34 ml) and water (100 ml) at 0°-5° C. This mixture was stirred at 0° to 10° C. (pH>9.5) for 1 hour, stirred at room temperature overnight and then stirred at 40-45° C., pH 9.5 for 1 hour. The temperature of the mixture was increased to 80-85° C., the pH adjusted to 11.5 with NaOH solution and then the mixture was stirred for 3 hours. At the end of this time the mixture was cooled to room temperature and pH lowered to 9 with HCl solution. Reaction filtered and filtrate evaporated to low volume and product precipitated by addition of methanol (700 ml). The solid which precipitated was filtered, dissolved in deionised water, dialysed, filtered and then dried at 70° C. to give 8.3 g of product.

COMPARATIVE EXAMPLE 1 AND 2

Comparative Example 1 was PRO-JET™ Cyan 1 (C.I. Direct Blue 199) and Comparative Example 2 was PRO-JET™ Cyan 2 both obtained from Avecia Ltd. PRO-JET™ Cyan 1 and PRO-JET™ Cyan 2 are two of the leading ink-jet phthalocyanine dyes.

Preparation of Ink 1 and the Comparative Inks

The dye of Example 1 and the dyes of Comparative Example 1 and Comparative Example 2 were converted into inks by dissolving 1 g of the dye in 19 g of a liquid medium comprising:

| | |
|---|---|
| Thiodiethylene glycol | 5% |
| 2-Pyrrolidone | 5% |
| Surfynol ™ 465 | 1% |
| Water | 89% |
| | (all % by weight) | and adjusting the pH of the ink to 8-10 using sodium hydroxide.

Surfynol™ 465 is a surfactant from Air Products.

Ink-jet Printing

Inks prepared as described above were filtered through a 0.45 micron nylon filter and then incorporated into empty print cartridges using a syringe.

These inks were then printed onto Xerox 4024 Premium Multipurpose White Paper (Xerox 4024), HP Premium Plus Photo Paper (HPPP), Epson Premium Glossy Photopaper ("SEC PM") and Canon PR101 Photopaper (PR101).

The prints so formed were tested for ozone fastness by exposure to 1 ppm ozone at 40° C., 50% relative humidity for 24 hrs in a Hampden 903 Ozone cabinet. Fastness of the printed ink to ozone can be judged by the difference in the optical density before and after exposure to ozone.

Light-fastness of the printed image was assessed by fading the printed image in an Atlas Ci5000 Weatherometer for 100 hours and then measuring the change in the optical density.

Optical density measurements are performed using a Gretag spectrolino spectrophotometer set to the following parameters:

| | |
|---|---|
| Measuring Geometry | 45°/0° |
| Spectral Range | 380-730 nm |
| Spectral Interval | 10 nm |
| Illuminant | D65 |
| Observer | 2° (CIE 1931) |
| Density | Ansi A |
| External Filler | None |

Light and Ozone fastness were assessed by the percentage change in the optical density of the print, where a lower figure indicates higher fastness, and the degree of fade. The degree of fade is expressed as ΔE where a lower figure indicates higher light fastness. ΔE is defined as the overall change in the CIE colour co-ordinates L, a, b of the print and is expressed by the equation $\Delta E=(\Delta L^2+\Delta a^2+\Delta b^2)^{0.5}$.

Results for the light and ozone fastness of prints formed from the test and comparative inks with different media are shown in Tables 1 to 4.

TABLE 1

Light Fastness - Percentage Optical Density Loss

| Ink | Xerox 4024 | HPPP | SEC PM | PR101 |
|---|---|---|---|---|
| Ink 1 | 5 | 36 | 13 | 11 |
| Comparative Ink 1 | 19 | 26 | 19 | 15 |
| Comparative Ink 2 | 10 | 32 | 33 | 47 |

TABLE 2

Light Fastness - ΔE

| Ink | Xerox 4024 | HPPP | SEC PM | PR101 |
|---|---|---|---|---|
| Ink 1 | 4 | 16 | 3 | 7 |
| Comparative Ink 1 | 13 | 11 | 6 | 8 |
| Comparative Ink 2 | 10 | 13 | 12 | 21 |

TABLE 3

Ozone Fastness - Percentage Optical Density Loss

| Ink | SEC PM | PR101 |
|---|---|---|
| Ink 1 | 13 | 7 |
| Comparative Ink 1 | 41 | 43 |
| Comparative Ink 2 | 41 | 40 |

TABLE 4

Ozone Fastness - ΔE

| Ink | SEC PM | PR101 |
|---|---|---|
| Ink 1 | 5 | 3 |
| Comparative Ink 1 | 18 | 22 |
| Comparative Ink 2 | 17 | 18 |

Further Inks

The inks described in Tables A and B may be prepared using the Compound made in the above Example. Numbers quoted refer to the number of parts of the relevant ingredient and all parts are by weight. The inks may be applied to paper by thermal, piezo or any other type of ink-jet printing.

The following abbreviations are used in Tables A and B:
PG=propylene glycol
DEG=diethylene glycol
NMP=N-methylpyrrolidone DMK=dimethylketone
IPA=isopropanol
MEOH=methanol
2P=2-pyrrolidone
MIBK=methylisobutyl ketone
P12=propane-1,2-diol
BDL=butane-2,3-diol
CET=cetyl ammonium bromide
PHO=Na$_2$HPO$_4$ and
TBT=tertiary butanol
TDG=thiodiglycol

TABLE A

| Dye Content | Water | PG | DEG | NMP | DMK | NaOH | Na Stearate | IPA | MEOH | 2P | MIBK |
|---|---|---|---|---|---|---|---|---|---|---|---|
| 2.0 | 80 | 5 | | 6 | 4 | | | | | 5 | |
| 3.0 | 90 | | 5 | 5 | | 0.2 | | | | | |
| 10.0 | 85 | 3 | | 3 | 3 | | | | 5 | 1 | |
| 2.1 | 91 | | 8 | | | | | | | | 1 |
| 3.1 | 86 | 5 | | | | 0.2 | | 4 | | | 5 |
| 1.1 | 81 | | | 9 | | 0.5 | 0.5 | | | 9 | |
| 2.5 | 60 | 4 | 15 | 3 | 3 | | | 6 | 10 | 5 | 4 |
| 5 | 65 | 20 | | | | | | 10 | | | |
| 2.4 | 75 | 5 | 4 | | 5 | | | | 6 | | 5 |
| 4.1 | 80 | 3 | 5 | 2 | 10 | | 0.3 | | | | |
| 3.2 | 65 | | 5 | 4 | 6 | | | 5 | 4 | 6 | 5 |
| 5.1 | 96 | | | | | | | | 4 | | |
| 10.8 | 90 | 5 | | | | | | 5 | | | |
| 10.0 | 80 | 2 | 6 | 2 | 5 | | | 1 | | 4 | |
| 1.8 | 80 | | 5 | | | | | | | 15 | |
| 2.6 | 84 | | | 11 | | | | | | 5 | |
| 3.3 | 80 | 2 | | | 10 | | | | 2 | | 6 |
| 12.0 | 90 | | | | 7 | 0.3 | | 3 | | | |
| 5.4 | 69 | 2 | 20 | 2 | 1 | | | | | 3 | 3 |
| 6.0 | 91 | | | 4 | | | | | | 5 | |

TABLE B

| Dye Content | Water | PG | DEG | NMP | CET | TBT | TDG | BDL | PHO | 2P | PI2 |
|---|---|---|---|---|---|---|---|---|---|---|---|
| 3.0 | 80 | 15 | | | 0.2 | | | | | 5 | |
| 9.0 | 90 | | 5 | | | | | | 1.2 | | 5 |
| 1.5 | 85 | 5 | 5 | | 0.15 | 5.0 | 0.2 | | | | |
| 2.5 | 90 | | | 6 | 4 | | | | 0.12 | | |
| 3.1 | 82 | 4 | 8 | | 0.3 | | | | | | 6 |
| 0.9 | 85 | | 10 | | | | | 5 | 0.2 | | |
| 8.0 | 90 | | 5 | 5 | | | 0.3 | | | | |
| 4.0 | 70 | | 10 | 4 | | | | 1 | | 4 | 11 |
| 2.2 | 75 | 4 | 10 | 3 | | | | 2 | | 6 | |
| 10.0 | 91 | | | 6 | | | | | | 3 | |
| 9.0 | 76 | | 9 | 7 | | 3.0 | | | 0.95 | 5 | |
| 5.0 | 78 | 5 | 11 | | | | | | | 6 | |
| 5.4 | 86 | | | 7 | | | | | | 7 | |
| 2.1 | 70 | 5 | 5 | 5 | 0.1 | 0.2 | 0.1 | 5 | 0.1 | 5 | |
| 2.0 | 90 | | 10 | | | | | | | | |
| 2 | 88 | | | | | | 10 | | | | |
| 5 | 78 | | | 5 | | | 12 | | | 5 | |
| 8 | 70 | 2 | | 8 | | | 15 | | | 5 | |
| 10 | 80 | | | | | | 8 | | | 12 | |
| 10 | 80 | | 10 | | | | | | | | |

The invention claimed is:

1. A composition comprising:
(a) a major dye component which is a mixture of phthalocyanine dyes of Formula (1) and salts thereof:

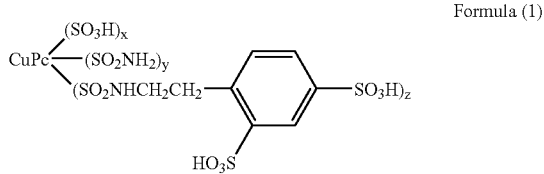

Formula (1)

wherein:
Pc represents a phthalocyanine nucleus of formula;

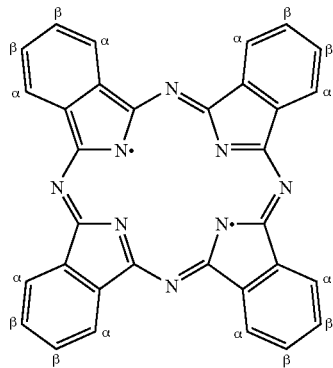

x is 0.4 to 1.5;
y is 0.1 to 3.8;
z is 0.1 to 3.8;
the sum of x+y+z is 3 to 4; and
the substituents, represented by x, y and z, are attached only to a β-position on the phthalocyanine ring; and
(b) a liquid medium.

2. A composition according to claim 1 wherein the mixture of dyes of Formula (1) are prepared by means of a cyclisation reaction comprising a β-substituted phthalic acid or analogue thereof.

3. A composition according to claim 2 wherein the β-substituted phthalic acid analogue is selected from the group consisting of phthalonitrile, iminoisoindoline, phthalic anhydride, phthalimide and phthalamide.

4. A composition according to claim 2 wherein x+y+z is 4.

5. A composition according to claim 2 wherein x has a value of 0.5 to 1.

6. A composition according to claim 2 wherein y has a value of 0.3 to 0.8.

7. A composition according to claim 2 wherein z has a value of 2.2 to 3.2.

8. A composition according to claim 2 which comprises:
(a) from 0.01 to 30 parts of a compound of Formula (1); and
(b) from 70 to 99.99 parts of a liquid medium;
wherein all parts are by weight.

9. A composition according to claim 8 wherein the number of parts of component (a) is from 0.5 to 15 parts and the number of parts of component (b) is from 85 to 99.5 parts.

10. A composition according to claim 9 wherein the number of parts of component (a) is from 1 to 5 parts and the number of parts of component (b) is from 95 to 99 parts.

11. A composition according to claim 2 which is ink suitable for use in an ink-jet printer.

12. A process for forming an image on a substrate comprising applying ink according to the claim 11 thereto by means of an ink-jet printer.

13. A material printed by means of a process according to claim 12.

14. An ink-jet printer cartridge comprising a chamber and an ink according to claim 11 wherein the ink is in the chamber.

15. A mixture of phthalocyanine dyes of Formula (1) and salts thereof:

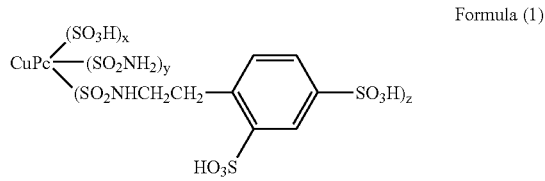

Formula (1)

wherein:
Pc represents a phthalocyanine nucleus of formula;

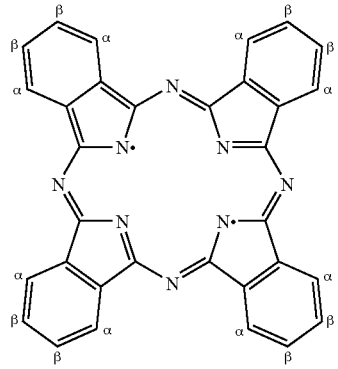

x is 0.4 to 1.5;
y is 0.1 to 3.8;
z is 0.1 to 3.8;
the sum of x+y+z is 3 to 4; and
the substituents, represented by x, y and z, are attached only to a β-position on the phthalocyanine ring.

16. A mixture of phthalocyanine dyes according to claim 15 prepared by means of a cyclisation reaction comprising a β-substituted phthalic acid or analogue thereof.

17. A mixture of phthalocyanine dyes of Formula (1) according to claim 16 prepared by cyclisation of 4-sulfophthalic acid and optionally phthalic acid.

18. A material printed with a mixture of phthalocyanine dyes of Formula (1) and salts thereof according to claim 15.

* * * * *